(12) United States Patent
Strnad et al.

(10) Patent No.: US 8,808,334 B2
(45) Date of Patent: Aug. 19, 2014

(54) ORTHOPEDIC PLATE

(75) Inventors: Lee A. Strnad, Broadview Hts, OH (US); David B. Kay, Akron, OH (US); Amanda Martin, Norton, OH (US); G. Martin Wynkoop, Gainesville, FL (US)

(73) Assignee: Orthohelix Surgical Designs, Inc., Medina, OH (US)

( * ) Notice: Subject to any disclaimer, the term of this patent is extended or adjusted under 35 U.S.C. 154(b) by 1580 days.

(21) Appl. No.: 11/714,023

(22) Filed: Mar. 5, 2007

(65) Prior Publication Data
US 2007/0239163 A1  Oct. 11, 2007

Related U.S. Application Data

(60) Provisional application No. 60/780,027, filed on Mar. 7, 2006.

(51) Int. Cl.
*A61B 17/80* (2006.01)

(52) U.S. Cl.
USPC .................................. 606/286; 606/280

(58) Field of Classification Search
USPC ............... 606/70–71, 280–299, 902–906
See application file for complete search history.

(56) References Cited

U.S. PATENT DOCUMENTS

| | | | | |
|---|---|---|---|---|
| 3,593,709 A | * | 7/1971 | Halloran | 606/283 |
| 4,988,350 A | * | 1/1991 | Herzberg | 606/65 |
| 5,197,966 A | | 3/1993 | Sommerkamp | |
| 5,304,180 A | * | 4/1994 | Slocum | 606/282 |
| 5,853,413 A | * | 12/1998 | Carter et al. | 606/281 |
| 6,096,040 A | * | 8/2000 | Esser | 606/280 |
| D443,060 S | * | 5/2001 | Benirschke et al. | D24/155 |
| 6,235,032 B1 | * | 5/2001 | Link | 606/280 |
| 6,235,034 B1 | | 5/2001 | Bray | |
| 6,283,969 B1 | * | 9/2001 | Grusin et al. | 606/280 |
| 6,358,250 B1 | | 3/2002 | Orbay | |
| 6,364,882 B1 | | 4/2002 | Orbay | |
| 6,508,819 B1 | | 1/2003 | Orbay | |
| D480,141 S | * | 9/2003 | Benirschke et al. | D24/155 |
| 6,623,486 B1 | | 9/2003 | Weaver et al. | |
| 6,712,820 B2 | | 3/2004 | Orbay | |

(Continued)

OTHER PUBLICATIONS

"The Spiral Compression Plate for Proximal Humeral Shaft Nonunion: a Case Report and Description of a New Technique" (Gill et al.) Journal of Orthopaedic Trauma: vol. 12(2). Feb. 1999. p. 141-144. Conclusion; Fig. 2 and 4.

(Continued)

*Primary Examiner* — Nicholas Woodall
*Assistant Examiner* — Larry E Waggle, Jr.
(74) *Attorney, Agent, or Firm* — Hudak, Shunk & Farine Co. LPA

(57) ABSTRACT

An orthopedic plate has a portion with a curved bottom surface that is designed to extend longitudinally along the bone and change the inferior curve as it advances proximally along the bone from a shallower to a sharper radius and further spirals downward as the plate advances. The plate includes a set of tabs, offset from the longitudinal axis of the plate to provide for better pullout values. The ears may be located at the terminal portion of the plate or somewhat more intermediate to the terminus of the plate, depending on the intended application. A point in the center of the central screw hole can be used to define the origin of the plate, and the angles of the screw and/or pegs holes can be referenced with Z, Y, and Z coordinates relative to this central hole.

16 Claims, 7 Drawing Sheets

(56) References Cited

U.S. PATENT DOCUMENTS

| | | | | |
|---|---|---|---|---|
| 6,932,842 | B1* | 8/2005 | Litschko et al. | 623/16.11 |
| 7,341,589 | B2* | 3/2008 | Weaver et al. | 606/291 |
| 7,537,604 | B2* | 5/2009 | Huebner | 606/281 |
| 8,177,818 | B2* | 5/2012 | Wotton, III | 606/280 |
| 2002/0183753 | A1* | 12/2002 | Manderson | 606/69 |
| 2004/0059334 | A1 | 3/2004 | Weaver et al. | |
| 2004/0102777 | A1* | 5/2004 | Huebner | 606/69 |
| 2004/0153073 | A1 | 8/2004 | Orbay | |
| 2004/0193155 | A1 | 9/2004 | Castaneda | |
| 2005/0065522 | A1 | 3/2005 | Orbay | |
| 2005/0080421 | A1 | 4/2005 | Weaver et al. | |
| 2005/0085818 | A1 | 4/2005 | Huebner | |
| 2005/0234458 | A1* | 10/2005 | Huebner | 606/69 |
| 2005/0245931 | A1 | 11/2005 | Orbay | |
| 2006/0173458 | A1* | 8/2006 | Forstein et al. | 606/69 |
| 2006/0259039 | A1 | 11/2006 | Pitkanen et al. | |

OTHER PUBLICATIONS

New Trauma Products from AO Development, Jun. 2006 (p. 9).

* cited by examiner

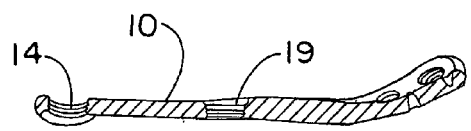
FIG.-7
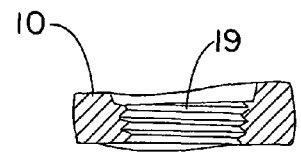
FIG.-7a
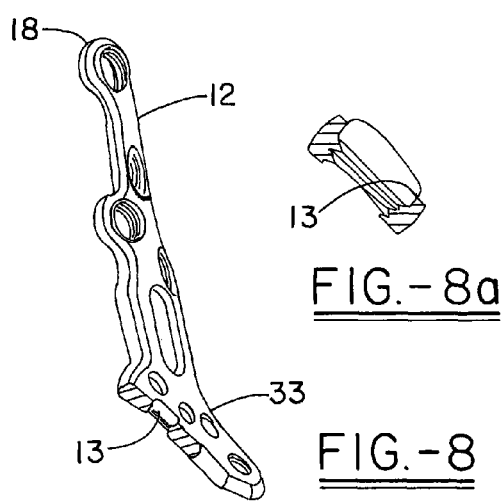
FIG.-8a
FIG.-8
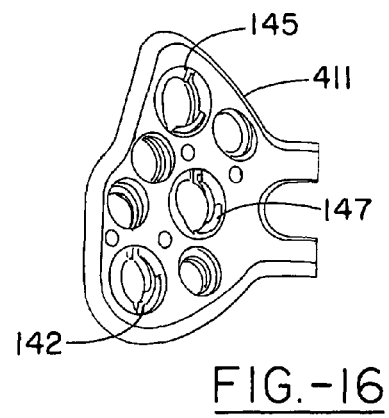
FIG.-16
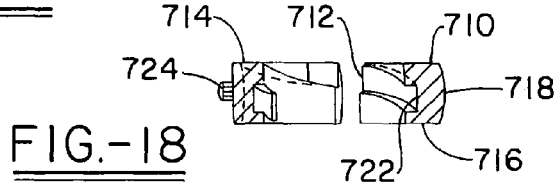
FIG.-18
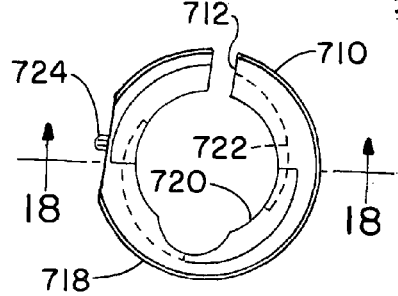
FIG.-17
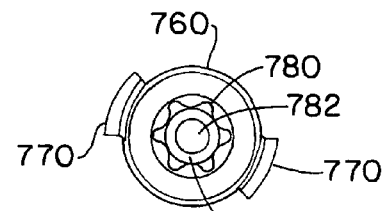
FIG.-20
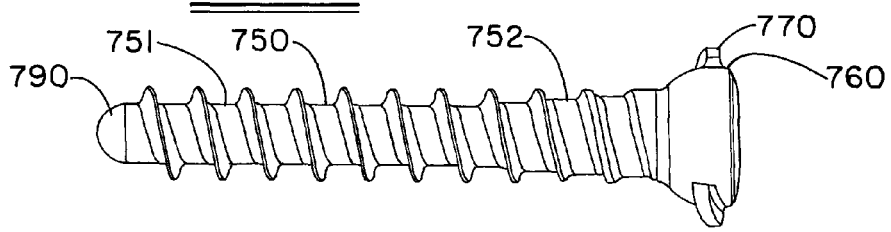
FIG.-19

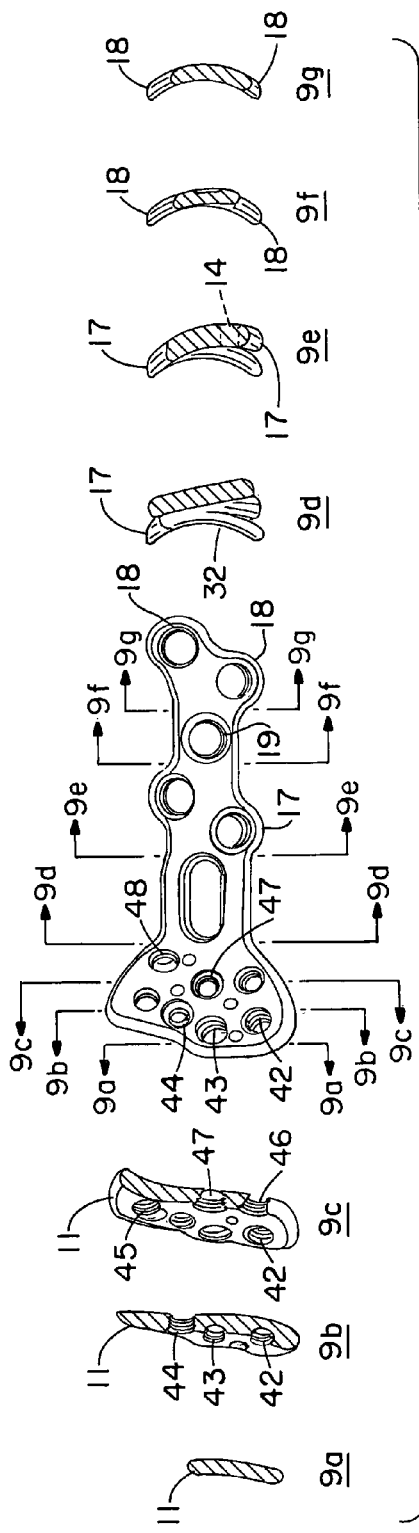
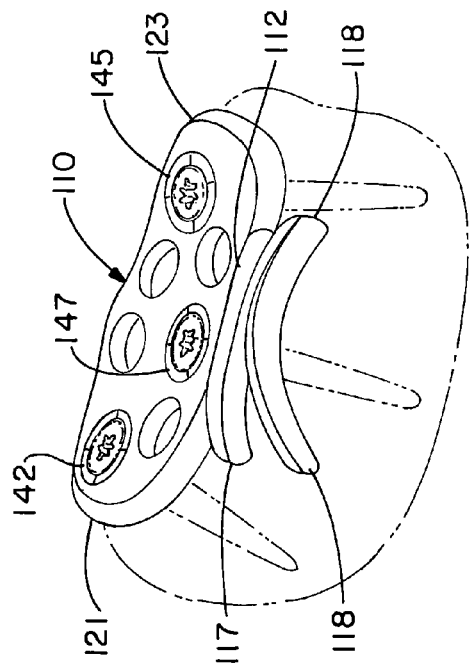
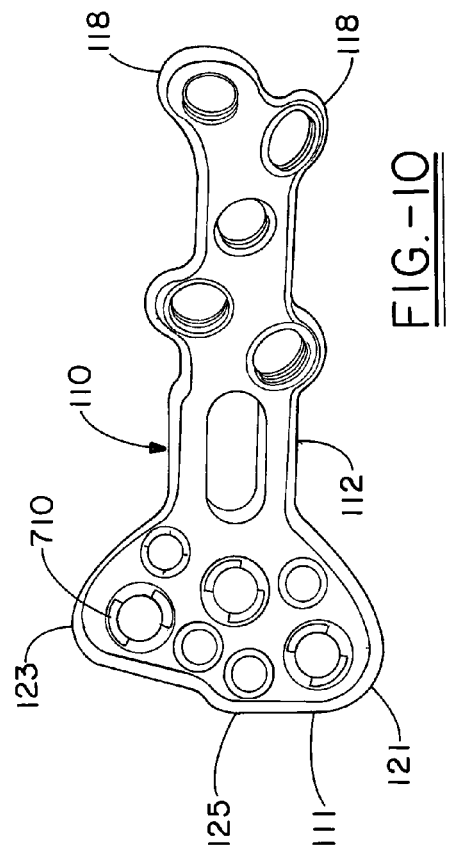

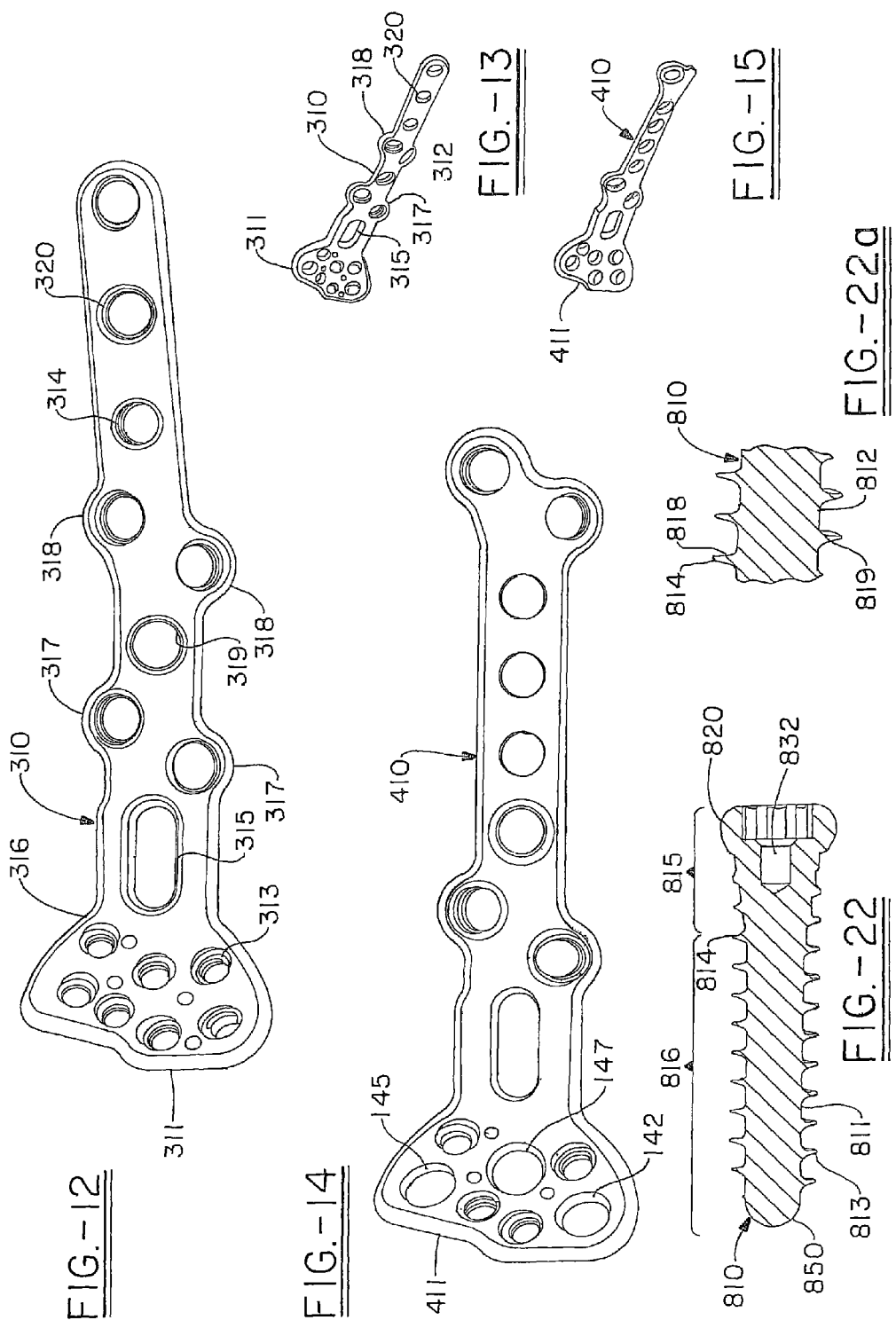

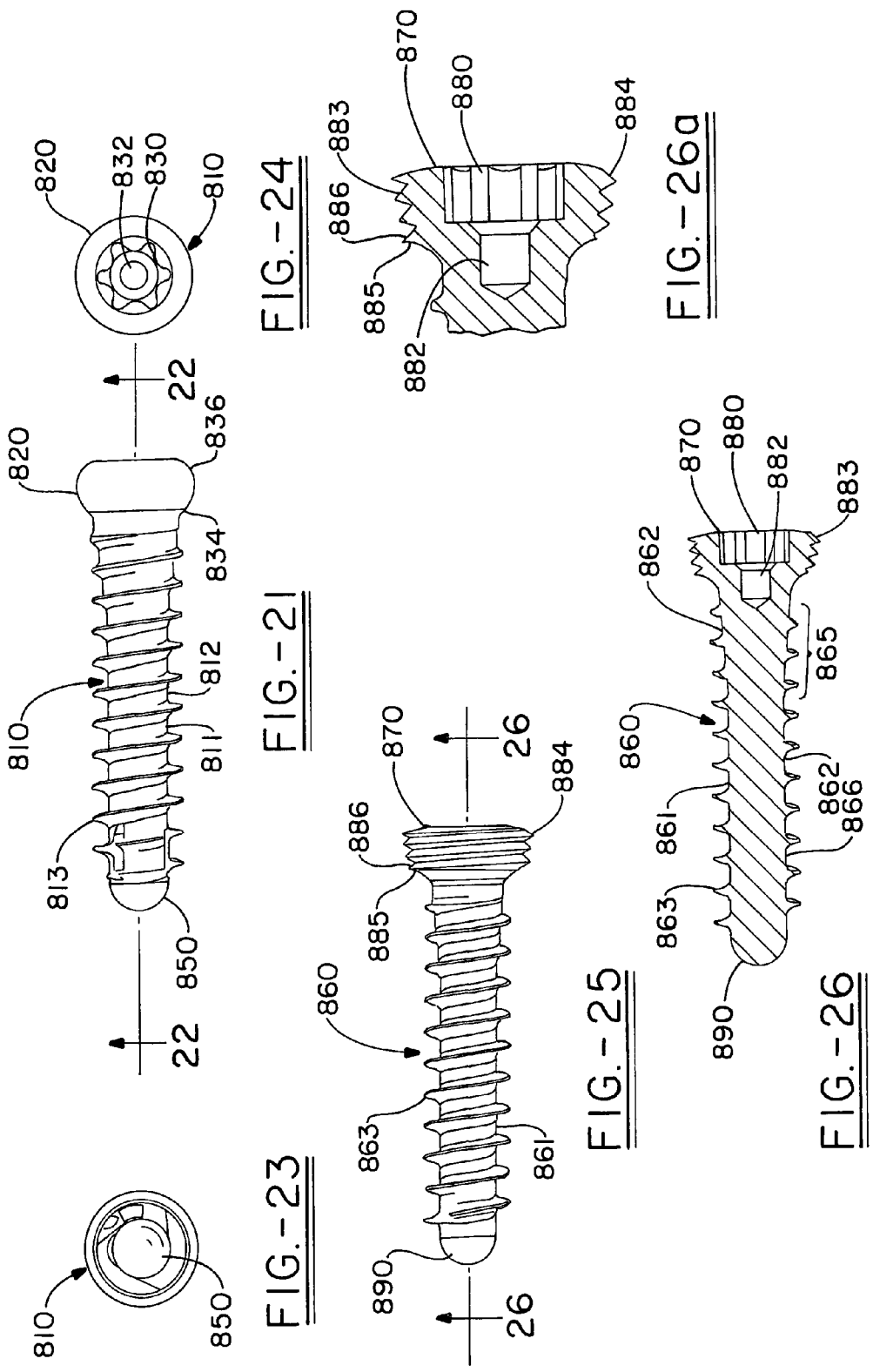

ORTHOPEDIC PLATE

This application is based on U.S. Provisional Application Ser. No. 60/780,027 filed on Mar. 7, 2006

FIELD OF THE INVENTION

The present invention relates to an orthopedic plate for fixation of bones. In particular it relates to a terminal section of an orthopedic plate that is useful for stabilization of small bones; for example, for a tibial plate for fixation of a tibial fracture, or for a distal radial plate for fixation of a distal radial fracture, or other fracture areas that can benefit from the design of the present invention.

BACKGROUND OF THE INVENTION

The ankle joint involves the intersection of the tibia, the fibula and the tarsals and metatarsals. The wrist is the joint formed at the intersection of the radius, the ulna, the carpals and the metacarpals. Both of these joints are designed to allow a great deal of freedom in the movement of the relevant appendage (i.e. the hand or foot). Attendant with this relative freedom, the joint itself is somewhat unstable, and easily subjected to trauma resulting in displacement or distortion within the bones of the joint, and in harm to the bones themselves. The wrist is the most frequently injured area of the upper extremity with three fourths of wrist injuries involving a fracture of the distal radius, and/or of the radius, and the ankle is subject to similar statistics with respect to the union of the tibia, the tarsals and the metatarsals. These injuries usually present in an emergency room setting, and often involve a fall for example for the wrist, onto an outstretched hand, and for the ankle, they involve a misstep onto a foot causing a rolling of the ankle. While the past conventional wisdom has included a belief that such injuries will tend to heal sufficiently on their own, there is often a loss of function and an early onset of arthritis that can be precipitated by the misdiagnosis and improper treatment of such injuries.

The treatments known for trauma to the extremities have included external stabilization and fixation such as by plaster casts, external fixators, and orthopedic plates. Casting alone, presents the possibility of misalignment of the fragments which can lead to severe loss of function and early onset of arthritis, if the fracture is not properly reduced, and/or if the fragments do not stay in a reduced state, in particular where the patient is not compliant. External fixators have been demonstrated to have an efficacy, but are cumbersome, cosmetically unappealing, and can lead to the possibility of infection at the attachment sites.

In order to avoid the foregoing problems, surgeons often consider methods of internal fixation, which typically include wire and/or screws, and plates. One issue presented by the use of wires is that a construct is time-consuming to construct; and screws alone, often do not provide the stability required for fusion of the fragments. Plates have the benefit of providing a construct that is designed for ease of implantation, and at the same time have the disadvantage that there is a significant variety in the shape and size of individual bones. Further, in particular, the tibia and radius bones are relatively small so that individual variations are relatively more significant than in larger bones, such as the femur, the pelvis, and the humerus. Moreover, the flesh surrounding the ankle joint is particularly dense with tendons, ligaments, nerves and blood vessels all of which are less forgiving of the intrusion of a metal construct than muscle or fatty tissue. This is also true for the wrist joint, particularly on the volar (or thumb) side.

SUMMARY OF THE INVENTION

The orthopedic plate of the present invention has a portion that is designed to extend longitudinally along the bone. This portion has an inferior curved surface which faces, or in some, but not necessarily all instances, touches the bone surface. More specifically, the curved surface is intended broadly to face the bone and to touch along its surface so as to support it on the surface of the plate (i.e. the surface facing the surface of the bone) so much as is allowed given the particular variations in individual bones. This portion of the plate changes this inferior curve as it advances proximally along the bone from a shallower to a sharper radius and further spirals downward toward the more advanced side of the plate. The more advanced side means the side which advances further along the longitudinal axis. Further, the plate in accordance with the invention has a plurality of screw holes, including one or more which are positioned along a central portion of the plate and further which preferably includes two or more which are offset from the central portion of the plate. The screw holes can be threaded so as to accept screws having threaded heads which will lock into position, or alternatively so that a screw with a smaller rounded smooth head can be screwed into the bone and mesh with the internal threads of the screw holes.

In a preferred embodiment, the plate includes a set of tabs or "ears" which are offset from the longitudinal axis of the plate, and further which allow the placement of screw holes that are offset from the longitudinal axis of the plate, as well as being offset longitudinally from each other. This allows the plate to be contoured about the circumference of the bone, and for the screws to be positioned at a convergent angle to provide for better pullout values, i.e. such that it requires a greater force to pull the screws from the bone. The ears may be located at the terminal portion of the plate or somewhat more intermediate to the terminus of the plate, depending on the intended application. The plate may also include an intermediate set of ears that similarly have a pair of offset intermediate threaded screw holes that are both longitudinally and laterally, or radially offset from the longitudinal axis of the plate, and which accept screws so as to have their axes at convergent angles. Again, the feature provides for better pullout values, and helps to avoid interference of the screws in the bone. In this instance, the plate includes a central screw hole which is located between the proximal pair of ears, and the intermediate pair of ears. This screw hole is preferably positioned so that the axis forms a right angle relative to the longitudinal axis of the plate, and further relative to a lateral axis through the hole. Thus, a point in the center of the central screw hole can be used to define the origin of the plate, and the angles of the screw and/or pegs holes can be referenced with X, Y, and Z coordinates relative to this central hole. Further, the topography of the head can be defined using this coordinate system, which permits the manufacture of the plate using computer generated imaging.

Distal to the intermediate pair of ears, the plate includes a slot which is radiused at either end to accept a screw having a head of the same dimensions as the threaded screw holes. The slot is elongated along the longitudinal axis of the plate. This allows the plate to be loosely attached by inserting a screw through the slot, and prior to tightening the plate can be slid in the longitudinal direction to allow the plate to be optimally positioned on the bone. The slot also allows the bone to be viewed through the plate preferably in the vicinity of the fracture.

In one embodiment, the plate of the invention may include a portion or head having a profile which flares from the sides of the plate to a leading edge that includes a central oblique linking area. This embodiment is designed expressly for use in the distal radius and the oblique linking area is designed to help to mark the placement of the plate relative to the radius. The head is shaped like a heart where the lobes have been asymmetrically truncated, like the palm of a hand, or like a modified kidney shape. Further in this embodiment, the head has a complex topography in the Z direction which echoes a generalized shape for the distal volar surface of a radius. The lunate prominence of the head has a lower elevation in the Z direction than the elevation of the styloid prominence in the direction relative to the radius. The longitudinal axis at the center of the proximal portion of the bone defines the Y direction, and the X direction extends transverse in a direction in which the bone widens. Further, the plate includes an oblique depression, or cup, that extends from the rounded pinky side of the head and gradually morphs into the elevated styloid prominence in one diagonal direction, and rises less gradually upward into the lunate prominence on the other side of the head. This distal cup undulates to define a superficial (i.e. relative to its surface) serpentine as it links into the proximal portion of the plate. The head preferably includes holes for pegs or screws which may be fixed, or variable. In other embodiments, such as for the distal tibias, the plate may include a corresponding head portion which is designed specifically to support the ankle joint at the union of the tibia, fibula, the tarsals and the metatarsals. Similarly, designs for other indications may include other head shapes, or none at all, so that the plate is straight, or even symmetrical from the top view about an axis transverse to the longitudinal axis of the plate. In the Z direction, the plate mimics the reverse spiral of the radial bone as it extends proximally away from the distal portion. Thus, the proximal portion of the plate appears to twist or spiral along the longitudinal axis, and includes a greater radial bend as it extends proximally since the bone becomes smaller and more circular in cross-section.

BRIEF DESCRIPTION OF THE DRAWINGS

FIG. 7 is a section of the plate taken along line 7 of FIG. 1;

FIG. 7a is a detail of the screw hole of FIG. 7;

FIG. 8 is a view from the side of the lunate prominence with the plate head in a lowered orientation and viewing the head in partial section to illustrate the detail of the threads of the peg holes;

FIG. 8a is a detail of the peg holes from FIG. 8;

FIG. 9 is a top view of the plate of FIG. 1 showing the lines at which the lateral sections of FIGS. 9a through 9g;

FIG. 9a is a section in the Y direction taken at line 9a of FIG. 9;

FIG. 9b is a section in the Y direction taken at line 9b of FIG. 9;

FIG. 9c is a section in the Y direction taken at line 9c of FIG. 9;

FIG. 9d is a section in the Y direction taken at line 9d of FIG. 9;

FIG. 9e is a section in the Y direction taken at line 9e of FIG. 9;

FIG. 9f is a section in the Y direction taken at line 9f of FIG. 9;

FIG. 9g is a section in the Y direction taken at line 9g of FIG. 9;

FIG. 10 is a top view of a second embodiment of the distal radius plate of the present invention;

FIG. 11 is a view from the proximal portion of the radial bone showing the plate in accordance with the present invention in position on the volar side of the bone and illustrating the angles for the pegs;

FIG. 12 is a top view of a third embodiment of the distal radial plate of the present invention with fixed angle pegs, and having an extended proximal portion;

FIG. 13 is a side perspective view of the plate of FIG. 12;

FIG. 14 is a top view of a fourth embodiment of the distal radial plate of the present invention with both fixed angle and variable angle locking pegs, and having an different embodiment of the extended proximal portion;

FIG. 15 is a side perspective view of the plate of FIG. 14;

FIG. 16 is a detail of the head of the distal radial plate of FIG. 14 showing the locking cam inserts in position in the peg holes of the head;

FIG. 17 is a top view of the locking cam insert used in the variable axis embodiment shown in FIGS. 10, 14 and 15;

FIG. 18 is a cross section of the locking cam insert of FIG. 17;

FIG. 19 is a side view of a variable axis locking screw for use with the embodiment shown in FIGS. 10, 14 and 15;

FIG. 20 is a top view of the variable axis locking screw of FIG. 19;

FIG. 21 is a side view of a non-locking screw that can be used as part of the plate system of the present invention;

FIG. 22 is a cross section of the non-locking screw of FIG. 21 taken along line 22 of FIG. 21;

FIG. 22a is a detail of the thread of FIG. 22;

FIG. 23 is an end view of the insertion tip of the screw of FIG. 21;

FIG. 24 is an end view of the torque receiving recess of the head of the screw of FIG. 21;

FIG. 25 is a side view of a locking screw that can be used as part of the plate system of the present invention;

FIG. 26 is a cross section of the non-locking screw of FIG. 25 taken along line 26 of FIG. 25;

FIG. 26a is a detail of the head of FIG. 26;

DETAILED DESCRIPTION OF THE INVENTION

The present invention relates to an orthopedic plate that can be used to stabilize the fracture of bone such as a radial bone, and in particular to the longitudinally extending plate portion, which tends to be placed proximally to the head, in the event that there is one.

Figure 1:
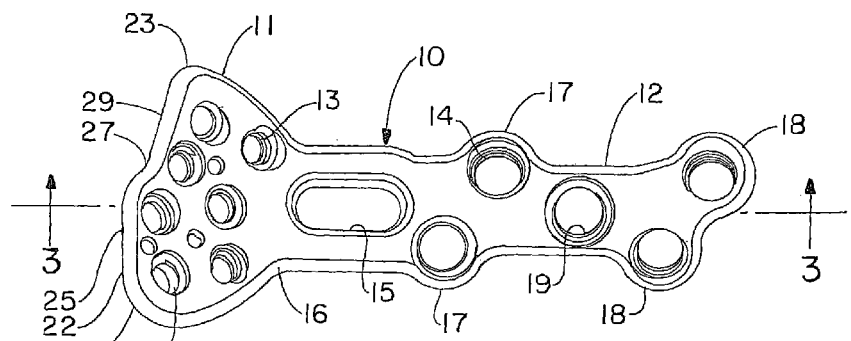
FIG. 1 is a top view of an orthopedic plate and plate head in accordance with a first embodiment of the invention for use on a left distal radius.
Figure 3:
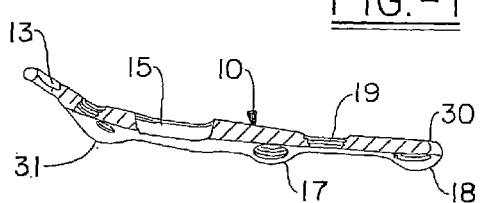
FIG. 3 is a cross section of the plate of FIG. 1 taken along line 3-3 in FIG. 1.
Figure 2:
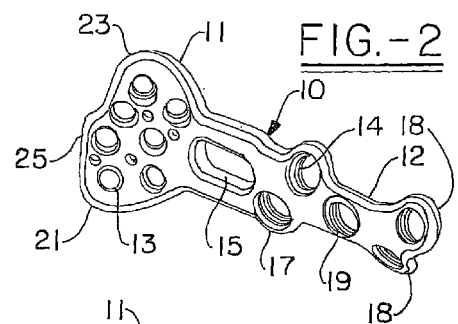
FIG. 2 is a perspective view of the plate of FIG. 1 viewed from the outer proximal surface looking toward the head with the styloid side of the plate downward.
Figure 3A:
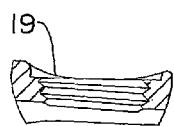
FIG. 3a is a detail of the central screw hole of FIG. 3.
Figure 4:
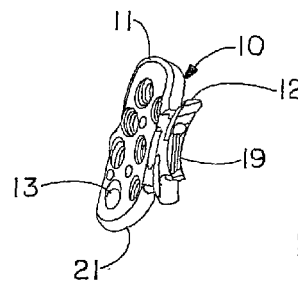
FIG. 4 is a cross section of the plate of FIG. 3 taken along line 4-4 in FIG. 3.
Figure 5:
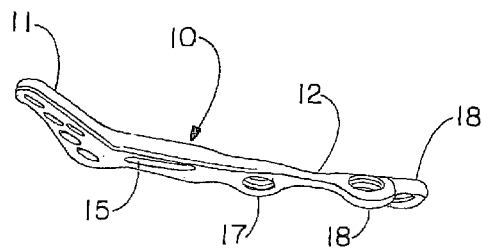
FIG. 5 is a view taken from the styloid side edge of the plate of FIG. 1.

A first embodiment of the plate is shown generally at 10 in FIG. 1 which includes a first, most distal portion or head 11 which has a profile from the top view similar to the palm of a hand, or which is shaped like a truncated heart, or a modified kidney shape. The head 11 slopes upward in a complex and organic topography away from the more elongated inversely curving proximal portion 12 of the plate. The head 11 includes a plurality of holes 13 for pegs, which holes can be internally threaded or not, or can also include means to provide for a variable locking axis. The proximal plate portion 12 also includes a plurality of holes 14 for screws, which similarly can include internal threads, or which can be smooth, or include means for a variable locking axis screw. The proximal portion of the plate also includes a slot 15 which is situated near the junction of the head 11 and the proximal portion of the plate, or the neck 16. The slot 15 can have a smooth internal edge, or can include a textured feature, such as grooves or tracks. The proximal portion also has two sets of tabs or ears, an intermediate pair 17 and a terminal pair 18 which each extend laterally from the longitudinal profile of the plate, and which provide for opposing screw holes that are each offset from the longitudinal axis of the plate and from each other along the longitudinal axis. The central point of a central screw hole 19 provides a point of reference or origin for mapping in three dimensions the topography or superficial locus of any point on the plate, which in turn enables the plate to be made having the complex curving fully contoured configuration that it does. The offset ears provide for convergence of the screws in the proximal or plate portion 12 of the distal radius plate while still avoiding screw interference so as to provide for improved pullout strength as compared to a version where the proximal screws are located along a line, such as the longitudinal axis.

As shown in this embodiment, the head portion 11 of the plate has a complex profile which is rounded on either side away from the neck area 16 to form a first prominence 21 and a second prominence 23. The first prominence 21 has a more gradual curve than the second prominence and is also the more distally extending of the two prominences. It is intended to support the radial styloid, and thus is termed the styloid prominence herein. The plate is provided in a left and a right version, which are mirror images of each other. The plate is generally intended to be implanted on the volar side of the radius (i.e. the top side when the arm is supine, and the palm is pointed upward). The styloid prominence 21 is thus on the lateral facing side of the plate, or the thumbward side. The second prominence 23 is designed to fit under the ridge of the lunate process, and is thus termed the "lunate" prominence herein. The distal edge 22 of the head 11 extends in a direction across the longitudinal axis of the proximal portion of the plate in three segments. A first portion 25 extends substantially transverse to the longitudinal axis of the plate to a point slightly more than, or about midway across the head of the plate. A second edge portion 27 links the first portion 25 and the third portion 29 and extends at an oblique angle proximally toward the third edge portion. The edge portion 27 or oblique link helps the surgeon to gauge the placement of the plate relative to the lunate ridge of the radial bone.

Figure 6:
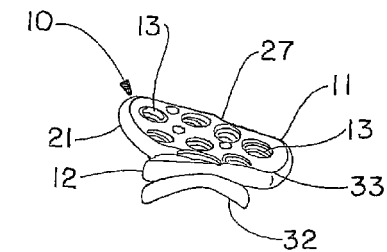
FIG. 6 is a view taken from the proximal edge of the plate of FIG. 1.

While the plate has tapering areas, the cross sectional dimension is generally sufficiently uniform that the contours of the top surface 30 generally mirror the contours of the bottom surface 31. In this context, "bottom" or "internal" is used to mean the surface which faces, and which may, but does not necessarily have to touch the bone, and "top" or "external" means the outwardly facing surface. These surfaces undulate to mimic the shape or topography of the radial bone. More specifically, the bottom surface of the proximal portion of the plate includes a concavity or radius 32 along the longitudinal axis where the thumb side of the plate has a greater arc than the pinky side. As might best be viewed in FIG. 8, the pinky side of the plate, (i.e., in that view, the right side) forms a shallow serpentine on both the top and bottom surfaces which defines a gentle depression or cup 33 which is followed by a rise toward the lunate prominence 23 of the head. The cup extends and becomes shallower as the plate surface rises toward the styloid prominence, which has the highest elevation in the Z direction. Thus, particularly in the proximal portion, the plate appears to spiral along the longitudinal axis of the radial bone. FIG. 6 further illustrates this aspect of the plate in accordance with the invention where the Y axis is taken through a central screw hole.

The topography of the plate is even more clearly shown in the sectional drawings FIGS. 9 through 9g which represent parallel slices taken in the Z planes at progressive locations along the longitudinal axis. It can be seen from these sections that the proximal portion 12 of the plate, as well as the head portion 11 of the plate is substantially non-planar, meaning that there is no significant portion of either the top surface or the bottom surface of either the proximal portion, or the head portion that defines a single plane. Instead, the head of the plate undulates from a central cup area that has a diagonal aspect from its lowest portion near the neck 16 of the plate on the pinky side of the head to the highest portion at the distal area on the styloid side of the plate. Thus, the top or exterior surface of the head 11 has a slightly concave area or cupped area 33 and other areas, such as the styloid prominence 21 and the lunate prominence 23 which are slightly convex on the top surface 30, or which rise. This transition can be said to cause the head to have top and bottom surfaces 30, 31 which undulate as they transition from the proximal portion of the plate 12 to the head portion 11. Further, the proximal portion of the plate 12 includes a bottom surface 31 which is radiused to fit the curve of the bone as it extends proximally from the wrist joint toward the elbow joint. This concave or radiused area changes as it extends along the longitudinal axis of the plate. In particular, the plate transitions from an area that is flatter in the vicinity of the neck 16, and which increases in the amount of curve as can be seen by comparing FIG. 9d through 9g which illustrate the cross-section of the plate at progressive proximal locations along the longitudinal axis. This topography is mirrored in the left and right versions of the plate, which are enantiomorphs (meaning that there is a three dimensional mirror symmetry) of each other. The plate spirals down the bone changing the internal curvature to accommodate the bone, and further changing the outline, or footprint that would be left on the bone by spiraling along the axis of the bone. Thus, the plate changes cross-section in the Z-direction, and also shifts in the X-Y directions to define this spiral.

The plate head 11 is further provided with a plurality of holes 13 which receive pegs that are implanted into the distal portion of the radius, or into fragments of the bone. In particular, the distal radius plate head of the present invention is presented in two embodiments. In a first embodiment, all of the holes define a fixed axis for the pegs which they receive. The pegs holes 13 include internal threads 3 which mate with locking threads on the head of the pegs and which therefore lock the pegs in position in the plate and which accordingly lock the bone relative to the plate. Of course, the plate could include peg holes which have no internal threads, or some combination of threaded and non-threaded holes. Alternatively, pegs can be used with a plate having threaded holes, where the pegs are not threaded at the top, but include a head that fits within the major diameter of the internal threads. In yet another embodiment, the pegs can be secured in the plate by means of a variable locking mechanism that allows the pegs to be inserted through the plate holes at a selected angle and to be subsequently locked into position at that angle. It is particularly preferred to provide a combination of locking pegs and variable locking pegs in the same head.

The holes include a distal hole 42 in the styloid prominence 21, and a hole in the lunate prominence 23 and one or more (two in the case shown) holes 43, 44 in the head intermediate to the two side holes. One or more proximal set of holes is also advantageously provided. For example, a hole 46 may be provided under the styloid hole 42 and a hole 48 may be provided proximal to the hole 45 in the lunate prominence 23, and a hole 47 may be provided between the hole 46 and the hole 48. The angles of these holes determine the angles of the pegs that they receive. The angles are defined on a three coordinate matrix where 0,0,0 is the origin and is located at the center of a central screw hole in the plate. Further, the plate is shown as including smaller diameter holes for K wires which help with the placement and angulation of the pegs. Thus, the holes K43-K48 have similar orientations to the holes 43-48 (where no K holes are illustrated for holes 42, 45 and 47). The angles are set to provide for the most common dislocation of fragments and to provide for the optimal fixation using the pegs.

The design contemplates a plurality of fixed peg holes, including one 42, 45 in each of the styloid (i.e. hole one) and lunate prominences (i.e. hole four), which splay outward and away from the plate such that they diverge away from one another to be capable of locking a styloid fragment and/or a fragment from the lunate fossa portion of the radial bone. A second distal-most hole 43 is located generally under the skewed linking area of the head, which defines a peg axis that extends through the radius and distally toward the scaphoid or navicular bone and a third hole 44 is distally aligned between the two holes of the prominences but is slightly backed off proximally from the second hole, with a peg axis that is more transverse than the peg axis of the second hole. The fourth peg hole 45 is the hole of the lunate prominence which is slightly more proximal than the first hole which is located in the styloid prominence. A fifth hole 46 is located in the first rounded side, which is on the styloid or thumbward side, toward the intersection between the proximal portion of the plate, and the plate head. The axis defined by this hole diverges outwardly toward the lateral portion of the radius (in a supine position). A sixth hole 47 is located in a central portion of the head such as on a longitudinal axis of the plate, and a final seventh hole 48 is located most proximally at the intersection of the head 11 and the proximal portion of the plate 12 at the neck 16 of the plate, with the axis of the peg appearing to be more or less transverse relative to the plane defined by the opening of the peg hole.

In a further embodiment of the invention, pegs or screws are included which have a variable axis with a locking mechanism. While this mechanism is illustrated for use in the head portion of the plate, is should be understood that it could be used in the proximal portion of the plate instead, or as well. FIGS. 10, 11, 14 through 20, illustrate this embodiment of the invention. In particular, one or more of the peg holes in the head portion 111 of the plate 110 of the first embodiment may be replaced with variable locking pegs, or the pegs may be reoriented. The proximal portion of the plate also includes a slot which is situated near the junction of the head 111 and the proximal portion of the plate, or the neck. The head 111 includes a styloid prominence 121 and a lunate 123 along with a portion of a distal edge of the plate 125. The proximal portion also has two sets of tabs or ears, an intermediate pair 117 and a terminal pair 118 which each extend laterally from the longitudinal profile of the plate, and which provide for opposing screw holes that are each offset from the longitudinal axis of the plate and from each other along the longitudinal axis. In the embodiment shown, holes 42, 45, and 47 are each replaced with a variable locking mechanism 142, 145, and 147. As one example of a variable locking mechanism, the one illustrated includes a camming mechanism on the head of the peg which mates with a cam locking insert that fits into and locks into a hole in the plate. The cam locking insert includes an anchor member that causes the cam locking insert to resist rotation as the camming members of the peg engage the cam raceway of the cam locking insert. Other variable locking mechanisms can be used with this invention, including other expansion inserts which mate with the holes in the plate at a variable angle, but can be locked in position, such as by expansion.

As an additional aspect of the invention, a distal radius plate is provided in an embodiment which has an elongated proximal portion. This design is illustrated in FIGS. 12 through 14 and is shown with a distal head having only fixed angle pegs and having both fixed and variable angle pegs. In the embodiment shown in FIGS. 12 and 13, the plate 310 has a distal portion, or head 311 and a proximal portion 312. The head portion includes pegs holes 313 which can be internally threaded so as to define screw holes having fixed axes as is shown in FIGS. 12 and 13, or as is illustrated in FIG. 11, and one or more of the fixed peg holes may be replaced with a variable axis mechanism, that advantageously also provides for locking of the angle of the axis. Again, it is envisioned that the proximal portion of the plate is provided in a right and a left version which are mirror images from each other.

The elongated version of the plate includes the features of the previously described version, with screw holes 314 in the proximal portion; an elongated slot 315 located along the central axis of the plate, adjacent the neck 316 which is the area that links the head 311, and the proximal portion 312. The elongated version of the plate further includes an intermediate tabbed area 317 having opposing offset ears that each receive a screw through an internally threaded screw hole, and a terminal tabbed area 318 that includes opposing offset ears that likewise each includes internally threaded screw holes. This version of the plate includes a central screw hole 319 that defines the origin for the coordinate system of the plate, and in addition, there are one or more additional longitudinally aligned screw holes 320. The elongated version of the plate has a proximal portion having a spiraling radiused portion similar to the shorter version except with a longer, and thus, more pronounced spiral. The fixed angle head 311 is the same as for the shorter version and the fixed angle head 11 of FIG. 1, and the head 411 of the plate 410 shown in FIGS. 14 and 15 is the same as the head 111 shown in FIGS. 10 and 16.

A camming insert is inserted in the variable axis bore holes, which have concavely rounded sides to permit variable angulation of the camming insert in the bore. The camming insert is a generally circular or ring shaped insert 710 having an expansion gap 712 which is essentially a planar slice taken in the insert so as to create a gap. The insert 710 has a top surface 714 which is generally planar joined to a co-planar bottom surface 716 by an outwardly curving side surface 718. There is a concentric inwardly curving surface 720 which further includes the cam race 722, which in this case are two grooves that spiral a portion of the way down and around the inside surface. The grooves are open, and preferably only for a portion of the top 714 where the grooves are located. This open area of the race allows the cams to be introduced into the race. Subsequently, as the screw or peg is turned in the camming insert, the cam engages the cam race and causes the insert to expand at the gap. This action causes the insert to lock in the recess (see FIG. 14, i.e. holes 142, 145 and 147) in the plate which receives the insert. Further, the insert 712 includes a stop 724. The stop is a projection that is received in a well in the recess which retains the stop 724 and prohibits the cam insert from turning with the peg as it is turned relative to the plate.

FIGS. 19 and 20 show a variable axis locking screw 750, which has a shaft 751 with a blunt or rounded insertion tip 790. The shaft 751 tapers throughout its length. The screw includes a locking head 760. The locking head includes a pair of cam wings 770 which are shaped to engage the race in the locking insert 710 and cause the insert to expand radially outwardly to form a friction fit in the bore hole and lock the camming insert in position in the bore. The shaft of the variable locking screw 750 is threaded with a thread 753 and having a taper to the minor diameter 752 of the shaft 751 over the first three to five turns of the thread toward the insertion tip 790 while the major diameter does not taper. The head 760 further includes a torque driving recess 780, with an optional bore 782 connected to the torque driving recess by a transitional area 781, which retains the screw 750 on the post of a screwdriver.

FIGS. 21 through 24 show a non-locking proximal screw 810, which is intended in particular for use in the proximal portion of the plate, when it is desirable that the screw does not lock into the plate. The screw 810 has a shaft portion 811 having a thread 813. The thread 813 shown in FIGS. 21 through 24 has a taper in the minor diameter 812 over a portion 815 of the shaft 811, such as about the first three turns of the thread. Thereafter, the terminal portion 816 of the shaft 811 has a constant minor diameter 812. The screw 810 has a blunt tip 850 and a rounded head 820 having a torque driving recess 830 optionally including a bore 832 to receive the post of a screwdriver to retain the screw on the screwdriver. The head has a spherically rounded lower portion 834 and a rounded upper portion 836 where the maximum outer diameter is smaller than the inner diameter of the threaded proximal screw holes. The shaft 811 has a minor diameter 812 about which the thread 813 spirals. The thread 813 includes a spiraling radial edge 814 best viewed in the thread detail FIG. 22a, which defines the major diameter. The thread further includes a front thrust face 818 which forms an angle of about 20°+/−5° to a plane transverse to the longitudinal axis of the screw. The trailing face 819 of the thread 813 forms an angle of about 5°+/−2° to the same plane.

FIGS. 25 through 26(a) show a locking proximal screw 860, which is intended in particular for use in the proximal portion of the plate when it is desirable that the screw locks into the plate. The screw 860 has a shaft portion 861 having a thread 863 similar to the thread previously shown. The thread 863 shown in FIGS. 25 and 26 has a taper in the minor diameter 862 over a portion 865 of the shaft 861, such as the first three turns of the thread. Thereafter, the terminal portion 866 of the shaft 861 has a constant minor diameter 862. The head of the screw 860 includes external locking threads 883 as can be best viewed in the head detail in FIG. 26a. These threads also include a radial edge 884, a front thrust face 885, and a trailing face 886. The angle of the front thrust face 885 is the same as the angle of the trailing face relative to a plane which transverses the longitudinal axis of the screw, and is about 30°+/−5° for each angle. Thus, the locking thread 883 on the head 870 of the screw is a symmetrical v-shaped thread when viewed in profile in cross section. The head 870 tapers along the longitudinal axis, in both the major and the minor diameter, by a similar amount, as is shown in FIG. 22a. For a proximal screw, the taper is about 7°, or about 3.5° per side when measured in cross-section. A larger screw might be used in the distal head of the plate and might have a taper of 20° or 10° per side in section.

The screw 860 has a blunt tip 890 and a rounded head 870 having a torque driving recess 880 optionally including a bore 882 to receive the post of a screwdriver to retain the screw on the screwdriver. The head has a locking thread 884 which tapers in both the major and minor diameter.

Figure 28:
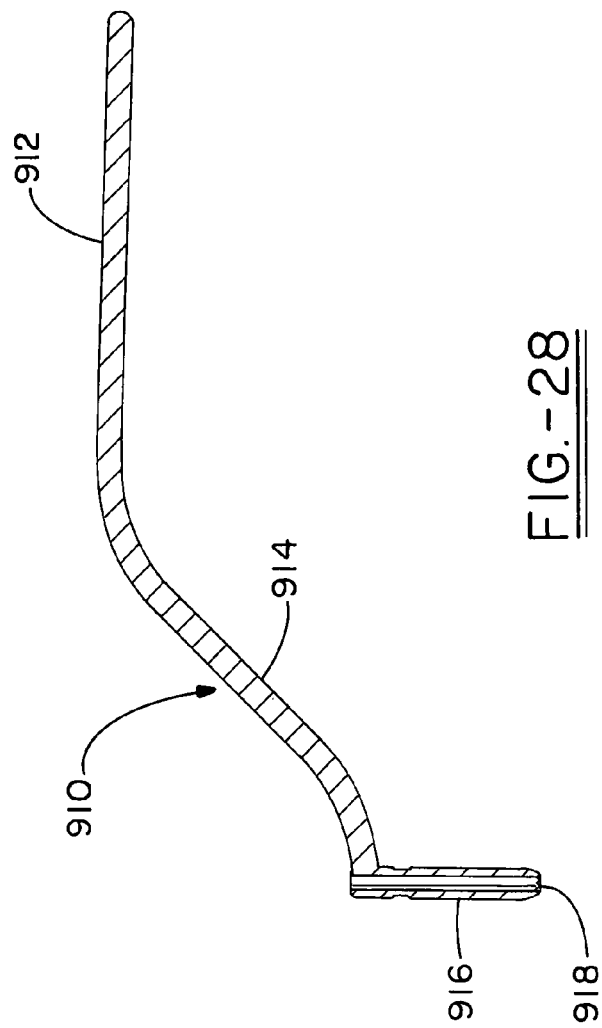
FIG. 28 is a cross section of the drill guide of FIG. 27.
Figure 27:
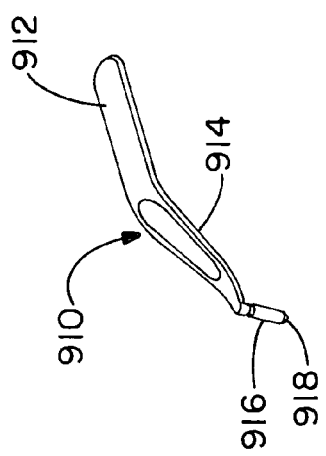
FIG. 27 is a top perspective view of a drill guide that can be used with the plate system of the present invention.
Figure 29:
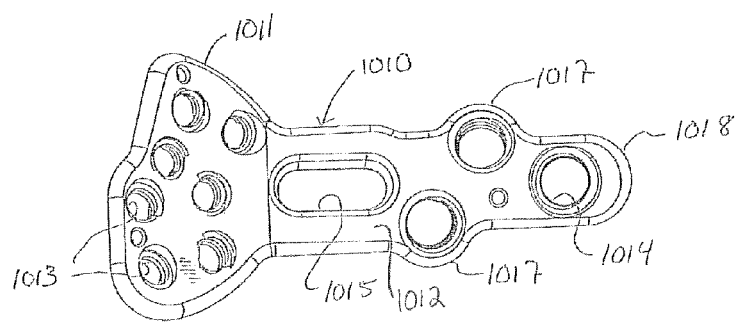
FIG. 29 is a top view of a short version of the orthopedic plate in accordance with the present invention.
Figure 30:
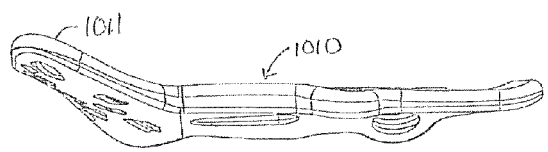
FIG. 30 is a first side view of the plate of FIG. 29.
Figure 31:
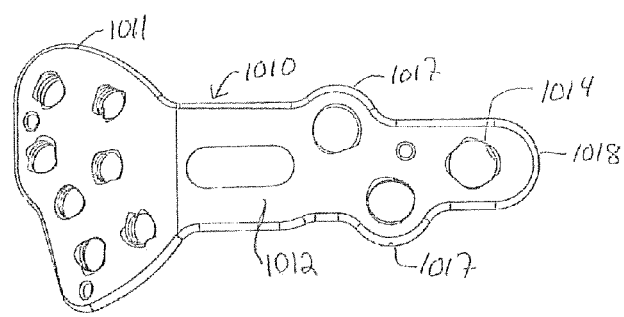
FIG. 31 is a bottom view of the plate of FIG. 29.
Figure 32:
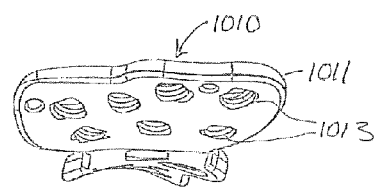
FIG. 32 is an edge view from the distal edge of the plate of FIG. 29.
Figure 33:
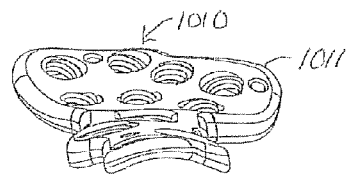
FIG. 33 is a edge view from the proximal edge of the plate of FIG. 29.
Figure 34:
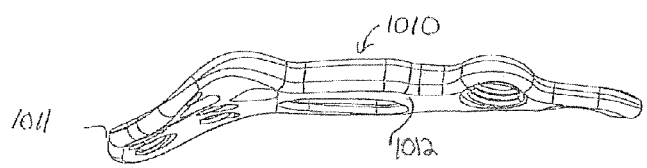
FIG. 34 is a second side view of the plate of FIG. 29.

FIGS. 27 and 28 show a drill guide for either the holes in the distal portion, or for the holes in the proximal portion. The drill guide 910 includes an extending handle 912 with a tapering linking portion 914 and a post 916 which engages the hole in the plate. The post 916 has an internal hole for the drill bit and can have a smooth tapered surface at the terminal end 918 which engages the hole of the plate by friction, or the post end 918 can include threads to lock into the internal threads of the plate and to fix the angle for the fixed screws.

FIGS. 29 through 34 show a further embodiment of the plate in accordance with the invention. This plate 1010 is comparable to the other embodiments in having a head 1011 joined to a proximal plate portion 1012. The head 1011 includes a plurality of peg holes 1013 as previously described and the proximal portion includes a plurality of screw holes 1014 and a compression slot 1015. This embodiment of the plate has only a single set of offset tabs 1017 which allows for convergent screws and the plate ends in a terminus 1018.

While in accordance with the patent statutes the best mode and preferred embodiment have been set forth, the scope of the invention is not limited thereto, but rather by the scope of the attached claims.

What is claimed is:

1. An orthopedic plate which is designed to extend along at least a portion of a bone in a direction proximal to distal so as to define a foot print the plate having an internal surface that is capable of opposing the bone in use, the plate having an external surface and an internal surface having an elongate portion and a head portion, at least a portion of the elongate portion defining a concavely curving area that changes from a shallower to a sharper radius as it advances in the proximal to distal direction, and wherein the footprint is not a bilaterally symmetrical footprint as it advances in the proximal to distal direction such that the internal surface defines a spiral, the plate further including a plurality of holes for fixation means that extend between the external surface and the internal surface.

2. An orthopedic plate as set forth in claim 1, further comprising: the plate having a complex curving fully contoured configuration that is generated using computer generated imaging and the elongate portion extending in a long direction so as to define a longitudinal axis in the long direction and having a top surface and a bottom surface wherein the bottom surface defines a first curve in cross section in a plane transverse to the longitudinal axis at a first point on the longitudinal axis and a second curve in cross section in a plane transverse to the longitudinal axis at a second point, said first point being spaced apart from said second point on said longitudinal axis to define a length and further where the configuration fluidly changes in cross-section for the length from the first curve to the second curve.

3. The orthopedic plate as set forth in claim 2, having at least one pair of holes that are offset from the longitudinal axis and which each define an axis through the center of the hole which together define a pair of axes that converge in the direction of the bottom of the plate.

4. The orthopedic plate as set forth in claim 3, wherein the plate has a first longitudinal side and a second longitudinal side and the plate further includes a pair of a first tab and a second tab which respectively project from the first longitudinal side and the second longitudinal side of the plate and each include one of said pair of offset holes.

5. The orthopedic plate as set forth in claim 4, further including a second pair of a first tab and a second tab which respectively project from the first longitudinal side and the second longitudinal side of the plate and the plate includes a second pair of offset holes and each of the second pair of tabs includes one of said second pair of offset holes.

6. The orthopedic plate as set forth in claim 2, wherein the head portion follows a different contour along the longitudinal axis.

7. The orthopedic plate as set forth in claim 2, wherein the plate curves along the longitudinal axis.

8. An orthopedic plate as set forth in claim 2, wherein the plate further includes a point which is used to define the origin of the plate with reference to X,Y, Z, coordinates and the topography of the plate is generated using this coordinate system.

9. An orthopedic plate as set forth in claim 1, further which includes holes that receive one or more of screws, pegs or wires the elongate portion extending in a long direction so as to define a longitudinal axis in a long direction so as to define a longitudinal axis and the internal surface having at least a portion which extends along the longitudinal axis and which defines a concave curve that changes in accordance with a topography generated by computer generated imaging as it advances along the longitudinal axis from a shallower to a sharper radius.

10. The orthopedic plate as set forth in claim 9, wherein the concave curve further spirals downward as the plate advances proximally.

11. The orthopedic plate as set forth in claim 10, further including a set of two tabs extending away from the longitudinal axis of the plate, each one of the tabs including a through hole and the mid point of each hole being offset from the longitudinal axis of the plate.

12. The orthopedic plate as set forth in claim 11, wherein a line connecting the mid point of each hole of the tabs is not transverse to the longitudinal axis of the plate.

13. The orthopedic plate as set forth in claim 12, further including one or more through holes aligned with the longitudinal axis of the plate.

14. The orthopedic plate as set forth in claim 9, wherein the head portion follows a different contour along the longitudinal axis.

15. The orthopedic plate as set forth in claim 14, wherein the head portion that includes a plurality of through holes for fixation means.

16. The orthopedic plate as set forth in claim 14, wherein the plate has a longitudinal axis and further includes a set of two tabs extending away from the longitudinal axis of the plate, each one of the tabs including a through hole and the mid point of each hole being offset from the longitudinal axis of the plate.

* * * * *